United States Patent
Jin et al.

(10) Patent No.: US 10,369,184 B2
(45) Date of Patent: Aug. 6, 2019

(54) COMPOSITION AND USE THEREOF IN MANUFACTURE OF PRODUCT FOR IMPROVING INTESTINAL FUNCTION

(71) Applicant: INFINITUS (CHINA) COMPANY LTD., Jiang Men (CN)

(72) Inventors: Xin Jin, Jiang Men (CN); Yazhong Ge, Jiang Men (CN); Chung Wah Ma, Jiang Men (CN); Chuixin Qin, Jiang Men (CN)

(73) Assignee: INFINITUS (CHINA) COMPANY LTD., Jiang Men (CN)

( * ) Notice: Subject to any disclaimer, the term of this patent is extended or adjusted under 35 U.S.C. 154(b) by 92 days.

(21) Appl. No.: 15/467,146

(22) Filed: Mar. 23, 2017

(65) Prior Publication Data

US 2018/0021399 A1     Jan. 25, 2018

(30) Foreign Application Priority Data

Jul. 21, 2016   (CN) .......................... 2016 1 0580563

(51) Int. Cl.
| | | |
|---|---|---|
| *A61K 36/8945* | (2006.01) | |
| *A61K 31/733* | (2006.01) | |
| *A61K 35/745* | (2015.01) | |
| *A61K 35/747* | (2015.01) | |
| *A61K 36/734* | (2006.01) | |

(52) U.S. Cl.
CPC ........ *A61K 36/8945* (2013.01); *A61K 31/733* (2013.01); *A61K 35/745* (2013.01); *A61K 35/747* (2013.01); *A61K 36/734* (2013.01)

(58) Field of Classification Search
None
See application file for complete search history.

(56) References Cited

U.S. PATENT DOCUMENTS 9,441,257 B2 *   9/2016   Choi .................... A23L 3/3463

FOREIGN PATENT DOCUMENTS

| CN | 102727819 | * 10/2012 | |
|---|---|---|---|
| WO | WO-2007125558 A1 | * 11/2007 | ........... A23C 9/1234 |

OTHER PUBLICATIONS

Machine translation CN 102727819, Oct. 2012.*
Abstract CN 102727819. Oct. 2012.*
Kong et al.,International Journal of Microbiology, vol. 2009, Article ID 598152, 13 pages.*

* cited by examiner

*Primary Examiner* — Renee Claytor
*Assistant Examiner* — Susan E. Fernandez
(74) *Attorney, Agent, or Firm* — Parker Highlander PLLC

(57) ABSTRACT

The present invention relates to the technical field of health care products, in particular to a composition and use thereof in the manufacture of a product for improving intestinal function. The present invention provides a composition and use thereof in the manufacture of a product for improving intestinal function. In the present invention, probiotics, prebiotics, *Crataegi Fructus* and *Dioscoreae Rhizoma* are reasonably compounded, wherein each component acts synergistically, thus allowing the obtained composition to have good effects of preventing and/or treating diarrhea as well as improving intestinal flora. The efficacy thereof is significantly superior to (P<0.05) that of the Comparative Examples.

9 Claims, No Drawings

COMPOSITION AND USE THEREOF IN MANUFACTURE OF PRODUCT FOR IMPROVING INTESTINAL FUNCTION

CROSS REFERENCE OF RELATED APPLICATIONS

The present application claims the priority of Chinese Patent Application No. 201610580563.1, filed with the Patent Office of China on Jul. 21, 2016, titled "COMPOSITION AND USE THEREOF IN MANUFACTURE OF PRODUCT FOR IMPROVING INTESTINAL FUNCTION", the contents of which are incorporated herein by reference in its entirety.

FIELD OF THE INVENTION

The present invention relates to the technical field of health care product, in particular to a composition and use thereof in the manufacture of a product for improving intestinal function.

BACKGROUND OF THE INVENTION

Diarrhea is a common disease which has always disturbed the human health for a long time. With the leaped changes in the life style of human in modern times, human intestinal flora have been, to some extent, difficult to adapt the modern life style, and all the changes in various stresses, dietary patterns and food habits have produced adverse effects on the spleen-stomach and intestinal microecology, thereby influencing the normal intestinal function.

In the traditional Chinese medicine, the spleen-stomach is believed to be the source of qi-blood metaplasia and the acquired foundation. The spleen functionally governs transportation and transformation while the stomach governs descending, both of which are associated with digestion, absorption, excretion and metabolism processes. When the spleen disfunctions in transportation, a diarrhea will occur, and thus it is believed in the traditional Chinese medicine that the sources of diarrheas all originate from the spleen-stomach. With studies of modern medicines, it has been found that a diarrhea induced by spleen deficiency is usually accompanied with disturbances in the intestinal flora. The spleen deficiency leads to digestion and absorption obstacles, the occurrence of poor appetite, loose stools, emaciation, etc., and destroys the balance between visceral organs in the body, which certainly will lead to disturbances in the intestinal flora, while the disturbances in the flora will in turn exacerbate the spleen deficiency, wherein they are cause and effect mutually. On one hand, in the diarrhea induced by spleen deficiency, the intestinal tract disfunctions, the intestinal peristalsis is accelerated, the stool frequency is increased, and beneficial anaerobes are discharged, resulting in the disturbances in the intestinal flora. On the other hand, in the spleen deficiency, the body's resistance is decreased, external toxic bacteria are extremely easy to invade and reproduce, exacerbating the disturbances in the intestinal flora. A vicious cycle is thereby formed, exacerbating the diarrhea and abdominal distension.

Antibiotic-associated diarrhea (AAD) refers to the most common iatrogenic diarrhea which is induced by disturbances in the intestinal flora occurred after clinical use of an antibiotic to treat an infectious disease. Since the advent of the antibiotic in 1940's, it has significantly reduced the mortality and complications from bacterial infections, which has played a huge role in the human health and development. However, the popularization and abuse of antibiotics today bring about many adverse effects. While killing the harmful bacteria in the body, antibiotic drugs will also kill the beneficial bacteria in the body, destroying the microecological balance in the intestinal tract, resulting in disturbances in the intestinal flora and thus a diarrhea.

Currently, most of medicines for treating a diarrhea are Western medicines which have obvious side effects and limited efficacies and which usually cure the symptoms rather than the disease. Therefore, it is of very important significance to further develop a product which is capable of improving and/or preventing a diarrhea, and capable of regulating the intestinal flora.

SUMMARY OF THE INVENTION

In view of these, the technical problem to be solved by the present invention is to provide a composition and use thereof in the manufacture of a product for improving intestinal function. The composition of the present invention is capable of effectively preventing and/or improving a diarrhea, and has a good effect of improving the intestinal flora.

The composition of the present invention comprises probiotics, prebiotics, *Crataegi Fructus* and *Dioscoreae Rhizoma*.

Probiotics are a class of active microorganisms beneficial to the host, and are the generic term of active and beneficial microorganisms which are colonized within the human intestinal tract and reproductive system, can produce a definite health efficacy to improve the microecological balance of the host, and play a beneficial role. In the present invention, the probiotics are selected from *Lactobacillus* and *Bifidobacterium*.

Among them, the *Lactobacillus* is a population of rod-shaped or spherical Gram-positive bacteria, which can allow sugar fermentation to produce plenty of lactic acid. The *Lactobacillus* is found in the human intestinal tract which is capable of acting on intestinal flora and can reduce the production of toxic substances in the intestinal tract, to allow the intestinal tract to keep a more stable environment, and also functions to adjust the immunity.

The *Bifidobacterium* is a Gram-positive, non-spore, anaerobic and multiform bacillus, which is a main microorganic resident bacterium in colonic microflora. The *Bifidobacterium* has been believed to be a microorganism which is safe and beneficial to human for a long time, from which the metabolites acetic acid and lactic acid have effects to improving intestinal function. Not only that, *Bifidobacterium* can also stimulate the specific immune ability, improve the immunity of the body, and also can improve symptoms of diarrhea.

In the present invention, the mass ratio of the *Lactobacillus* to the *Bifidobacterium* is (1.0~20.0):(1.0~20.0).

Wherein, the mass fraction of the *Lactobacillus* is 1.0%~20.0%, and the mass fraction of the *Bifidobacterium* is 1.0%~20.0%.

In embodiments of the present invention, the mass ratio of the *Lactobacillus* to the *Bifidobacterium* is (2.0~20.0):(2.0~20.0).

Wherein, the mass fraction of the *Lactobacillus* is 2.0%~20.0%, and the mass fraction of the *Bifidobacterium* is 2.0%~20.0%.

In some embodiments, the mass ratio of the *Lactobacillus* to the *Bifidobacterium* is 20.0:3.0.

In these embodiments, the mass fraction of the *Lactobacillus* is 20.0%, and the mass fraction of the *Bifidobacterium* is 3.0%.

In some embodiments, the mass ratio of the *Lactobacillus* to the *Bifidobacterium* is 10.0:5.0.

In these embodiments, the mass fraction of the *Lactobacillus* is 10.0%, and the mass fraction of the *Bifidobacterium* is 5.0%.

In some embodiments, the mass ratio of the *Lactobacillus* to *Bifidobacterium* is 7.0:12.0.

In these embodiments, the mass fraction of the *Lactobacillus* is 7.0%, and the mass fraction of the *Bifidobacterium* is 12.0%.

In some embodiments, the mass ratio of the *Lactobacillus* to the *Bifidobacterium* is 2.0:20.0.

In these embodiments, the mass fraction of the *Lactobacillus* is 2.0%, and the mass fraction of the *Bifidobacterium* is 20.0%.

In some embodiments, the mass ratio of the *Lactobacillus* to the *Bifidobacterium* is 2.0:2.0.

In these embodiments, the mass fraction of the *Lactobacillus* is 2.0%, and the mass fraction of the *Bifidobacterium* is 2.0%.

The amount of the probiotics added in the composition provided by the present invention is $10^6$ CFU/g~$10^{12}$ CFU/g.

The *Lactobacillus* used in the present invention has a bacterial density of no less than 10 billion CFU/g.

The *Bifidobacterium* used in the present invention has a bacterial density of no less than 10 billion CFU/g.

The prebiotics refer to a food component which cannot be absorbed by a host, but can selectively facilitate the growth and reproduction of one or more beneficial bacteria (probiotics) originally within the intestinal tract of the host and inhibit the growth of harmful bacteria, thus to achieve the regulation of intestinal flora and facilitate the body's health.

In the present invention, the mass fraction of the prebiotics is 30.0%~96.0%.

In embodiments of the present invention, the mass fraction of the prebiotics is 47.0%~90.0%.

In some embodiments, the mass fraction of the prebiotics is 47.0%.

In some embodiments, the mass fraction of the prebiotics is 65.0%.

In some embodiments, the mass fraction of the prebiotics is 48.0%.

In some embodiments, the mass fraction of the prebiotics is 50.0%.

In some embodiments, the mass fraction of the prebiotics is 90.0%.

In the present invention, the mass ratio of the probiotics to the prebiotics is (2.0~40.0):(30.0~96.0).

In embodiments of the present invention, the mass ratio of the probiotics to the prebiotics is (4.0~25.0):(47.0~90.0).

In some embodiments, the mass ratio of the probiotics to the prebiotics is 23.0:47.0.

In these embodiments, the mass mass fraction of the probiotics is 23.0%, and the mass mass fraction of the prebiotics is 47.0%.

In some embodiments, the mass ratio of the probiotics to the prebiotics is 15.0:65.0.

In these embodiments, the mass mass fraction of the probiotics is 15.0%, and the mass mass fraction of the prebiotics is 65.0%.

In some embodiments, the mass ratio of the probiotics to the prebiotics is 19.0:48.0.

In these embodiments, the mass mass fraction of the probiotics is 19.0%, and the mass mass fraction of the prebiotics is 48.0%.

In some embodiments, the mass ratio of the probiotics to the prebiotics is 22.0:50.

In these embodiments, the mass mass fraction of the probiotics is 22.0%, and the mass mass fraction of the prebiotics is 50%.

In some embodiments, the mass ratio of the probiotics to the prebiotics is 4.0:90.0.

In these embodiments, the mass mass fraction of the probiotics is 4.0%, and the mass mass fraction of the prebiotics is 90.0%.

In the present embodiments, the prebiotics is inulin.

Inulin, a naturally occurring component originated from chicory roots, is a naturally occurring oligosaccharide that is fructose, and is found in plants in a form of energy. Inulin is hardly hydrolyzed and digested by gastric acid, and thus the intact inulin is totally not destroyed before reaching the colon and is fermented by beneficial bacteria in the colon but cannot be utilized by most of the putrefactive bacteria, thus to keep the proliferation of probiotics within the intestinal tract under an advantageous condition, to maintain the heath of the intestinal tract and prevent diarrhea, etc.

The *Dioscoreae Rhizoma* and *Crataegi Fructus* have an efficacy to strengthen the spleen and stomach. The *Dioscoreae Rhizoma* is sweet, mid-natured, and has functions to tonify the spleen and nourish the stomach, to produce saliva and benefit the lung, and is useful for treating reduced appetite induced by spleen deficiency, diarrhea and loose stool. The *Crataegi Fructus* is sour and sweet, slightly warm-natured, and has functions to promote digestion and invigorate the stomach, to promote the qi circulation and dissipate blood stasis, and to treat dysentery and abdominal pains, which is useful for treating meat-type food accumulations and ungratifying diarrhea. The *Crataegi Fructus* powder is made by drying and pulverizing fresh *Crataegi Fructus*, with a particle size of 40 mesh; and the *Dioscoreae Rhizoma* powder is made by drying and pulverizing *Dioscoreae Rhizoma*, with a particle size of 40 mesh.

In the present invention, the mass ratio of the *Crataegi Fructus* to the *Dioscoreae Rhizoma* is (1.0~30.0):(1.0~30.0).

The mass fraction of the *Crataegi Fructus* is 1.0%~30.0%, and the mass fraction of the *Dioscoreae Rhizoma* is 1.0%~30.0%.

In embodiments of the present invention, the mass ratio of the *Crataegi Fructus* to *Dioscoreae Rhizoma* is (3.0~25.0):(3.0~25.0).

The mass fraction of the *Crataegi Fructus* is 3.0%~25.0%, and the mass fraction of the *Dioscoreae Rhizoma* is 3.0%~25.0%.

In some embodiments, the mass ratio of the *Crataegi Fructus* to the *Dioscoreae Rhizoma* is 25:5.0.

In these embodiments, the mass fraction of the *Crataegi Fructus* is 25%, and the mass fraction of the *Dioscoreae Rhizoma* is 5.0%.

In some embodiments, the mass ratio of the *Crataegi Fructus* to the *Dioscoreae Rhizoma* is 5.0:15.

In these embodiments, the mass fraction of the *Crataegi Fructus* is 5.0%, and the mass fraction of the *Dioscoreae Rhizoma* is 15%.

In some embodiments, the mass ratio of the *Crataegi Fructus* to the *Dioscoreae Rhizoma* is 8.0:25.

In these embodiments, the mass fraction of the *Crataegi Fructus* is 8.0%, and the mass fraction of the *Dioscoreae Rhizoma* is 25%.

In some embodiments, the mass ratio of the *Crataegi Fructus* to *Dioscoreae Rhizoma* is 3.0:25.0.

In these embodiments, the mass fraction of the *Crataegi Fructus* is 3.0%, and the mass fraction of the *Dioscoreae Rhizoma* is 25.0%.

In some embodiments, the mass ratio of the *Crataegi Fructus* to the *Dioscoreae Rhizoma* is 3.0:3.0.

In these embodiments, the mass fraction of the *Crataegi Fructus* is 3.0%, and the mass fraction of the *Dioscoreae Rhizoma* is 3.0%.

In the present invention, the probiotics, prebiotics, *Crataegi Fructus* and *Dioscoreae Rhizoma* are reasonably compounded, wherein each component acts synergistically, thus allowing the composition to have good effects of preventing and/or treating diarrhea as well as improving intestinal flora. The efficacy thereof is significantly superior to (P<0.05) that of the Comparative Examples (Comparative Example 1: only *Crataegi Fructus* and *Dioscoreae Rhizoma* are administered; Comparative Example 2: only probiotics and prebiotics are administered).

In the present invention, the mass ratio of the probiotics, the prebiotics, the *Crataegi Fructus* and the *Dioscoreae Rhizoma* is (2.0~40.0):(30.0~96.0):(1.0~30.0):(1.0~30.0).

In embodiments of the present invention, the mass ratio of the probiotics, the prebiotics, the *Crataegi Fructus* and the *Dioscoreae Rhizoma* is (4.0~25.0):(47.0~90.0):(3.0~25.0):(3.0~25.0).

In some embodiments, the mass ratio of the probiotics, the prebiotics, the *Crataegi Fructus* and the *Dioscoreae Rhizoma* is 23.0:47.0:25.0:5.0.

In these embodiments, the mass ratio of the probiotics is 23.0%, the mass ratio of the prebiotics is 47%, the mass fraction of the *Crataegi Fructus* is 25.0%, and the mass fraction of the *Dioscoreae Rhizoma* is 5.0%.

In some embodiments, the mass ratio of the probiotics, the prebiotics, the *Crataegi Fructus* and the *Dioscoreae Rhizoma* is 15.0:65.0:5.0:15.0.

In these embodiments, the mass fraction of the probiotics is 15.0%, and the mass fraction of the prebiotics is 65%, the mass fraction of the *Crataegi Fructus* is 5.0%, and the mass fraction of the *Dioscoreae Rhizoma* is 15.0%.

In some embodiments, the mass ratio of the probiotics, the prebiotics, the *Crataegi Fructus* and the *Dioscoreae Rhizoma* is 19.0:48.0:8.0:25.0.

In these embodiments, the mass fraction of the probiotics is 19.0%, the mass fraction of the prebiotics is 48%, the mass fraction of the *Crataegi Fructus* is 8.0%, and the mass fraction of the *Dioscoreae Rhizoma* is 25.0%.

In some embodiments, the mass ratio of the probiotics, the prebiotics, the *Crataegi Fructus* and the *Dioscoreae Rhizoma* is 22.0:50.0:3.0:25.0.

In these embodiments, the mass fraction of the probiotics is 22.0%, the mass fraction of the prebiotics is 50%, the mass fraction of the *Crataegi Fructus* is 3.0%, and the mass fraction of the *Dioscoreae Rhizoma* is 25.0%.

In some embodiments, the mass ratio of the probiotics, the prebiotics, the *Crataegi Fructus* and the *Dioscoreae Rhizoma* is 4.0:90.0:3.0:3.0.

In these embodiments, the mass fraction of the probiotics is 4.0%, the mass fraction of the prebiotics is 90%, the mass fraction of the *Crataegi Fructus* is 3.0%, and the mass fraction of the *Dioscoreae Rhizoma* is 3.0%.

It is believed in the traditional Chinese medicine that the spleen functionally governs transportation and transformation while the stomach governs descending, both of which are associated with digestion, absorption, excretion and metabolism processes. When the spleen disfunctions in transportation, a diarrhea will occur, and thus it is believed in the traditional Chinese medicine that the sources of diarrheas all originate from the spleen-stomach. With studies of modern medicines, it has been found that a diarrhea induced by spleen deficiency is usually accompanied with disturbances in the intestinal flora. The popularization and abuse of antibiotics today bring about many side effects. While killing the harmful bacteria in the body, antibiotic drugs will also kill the beneficial bacteria in the body, destroying the microecological balance in the intestinal tract, resulting in disturbances in the intestinal flora and thus a diarrhea. In the composition of the present invention, not only Chinese herbal medicines *Crataegi Fructus* and *Dioscoreae Rhizoma* which can strengthen the spleen and stomach, but also probiotics and prebiotics which can improve the intestinal flora are added, by which effects of improvement on and prevention of diarrhea as well as regulation of the intestinal flora are achieved by the rational combination and synergistic effect of the traditional Chinese medicines, probiotics and prebiotics.

Use of the composition provided by the present invention in the manufacture of a product for preventing and treating diarrhea.

The diarrhea prevented and treated by the composition of the present invention is antibiotic-associated diarrhea and/or diarrhea induced by spleen deficiency.

Experiments show that when using SD rats as the experimental subjects to establish rhubarb root and rhizome-induced spleen deficiency diarrhea model, fatigue and huddling, accidie, dull hair color, loose stool and other behaves occur during the establishment of models. 10 days after establishment of the models, the above symptoms in the model control group were relieved and the fecal characters of rats tended to be normal, while for the animals of Examples 1 to 7, the animal activities and the fecal characters were normal and the dietary and body weight were not significantly different from that of normal animal.

When using BALB/c mice as the experimental subjects to establish ampicillin-induced antibiotic-associated diarrhea model, the loose stool grade and index of diarrhea of the model control group were significantly different from that of the normal control group (P<0.05). Compared with the model control group, the loose stool grade and index of diarrhea of Comparative Examples 1-2 and Example 1, Example 4 and Example 5 were significantly decreased to some extent. The results show that the compositions provided by the present invention have synergistic effects and may improve the symptoms of antibiotic-induced diarrhea.

In the present invention, the dose of the composition provided by the present invention is 0.33 g/kg/d for preventing diarrhea.

That is, 0.33 g of the composition provided by the present invention is administered per kilogram of animal body weight per day. The animal is mouse or rat.

The present invention also provides a product for preventing and/or treating diarrhea, comprising the composition provided by the present invention.

The product for preventing and/or treating diarrhea is a health care product, a food or a medicament.

The health care product also comprises an acceptable excipient in health care product.

The medicament also comprises a pharmaceutically acceptable excipient.

The food also comprises an acceptable ingredient in food.

The health care product or medicament is an oral preparation, preferably a tablet, a capsule, a pill, a granule, a decoction, a paste, a distillate, an oral liquid, a dripping pill or a syrup.

Use of the composition provided by the present invention in the manufacture of a product for improving intestinal flora.

The composition provided by the present invention is capable of improving intestinal flora, that is, improving intestinal flora disorder induced by antibiotics administration and/or improving intestinal flora disorder induced by spleen deficiency.

In the present invention, the dose of the composition provided by the present invention is 0.33 g/kg/d for improving intestinal flora.

That is, 0.33 g of the composition provided by the present invention is administered per kilogram of animal body weight per day.

When using SD rats as the experimental subjects to establish rhubarb root and rhizome-induced spleen deficiency diarrhea model, the results of culture of the bacteria from the rat feces after the stop of the diarrhea show that, compared with the normal control group, the number of *Lactobacillus* and *Bifidobacterium* in the feces of spleen deficiency model rats were significantly decreased, and the number of *Clostridium perfringens* increased significantly; the control group administered with *Crataegi Fructus* powder and *Dioscoreae Rhizoma* powder could only significantly increase the number of *Lactobacillus* in the feces of model rats, but had no significant effect on other bacteria; Comparative Example 2, in which only probiotics and prebiotics were administered, can significantly increase the number of *Lactobacillus* and *Bifidobacterium* in the feces of the model rats, but had no significant effect on other bacteria; the combined sample group can significantly increase the number of *Lactobacillus* and *Bifidobacterium* in the feces of model rats, and the effect was significantly superior to that of Comparative Example 2. The result shows that the probiotics composition provided by the invention has a synergistic effect, can improve the symptoms of diarrhea induced by spleen deficiency, and effectively improve the balance of intestinal flora.

When using BALB/c mice as the experimental subjects to establish ampicillin-induced antibiotic-associated diarrhea model, the results of culture of the bacteria from the mice feces after the stop of the diarrhea shown that, compared with the normal control group, the number of *Lactobacillus* and *Bifidobacterium* in the feces of antibiotics model mice were significantly decreased, and the number of *Enterobacter, Enterococcus* and *Clostridium perfringens* were significantly increased; Comparative Example 1 can significantly increase the number of *Lactobacillus* and *Bifidobacterium* in the feces of the model mice, significantly reduce the number of *Enterococcus* and *Clostridium perfringens*, but had no significant effect on *Enterobacter*; Comparative Example 2 can significantly increase the number of *Lactobacillus* and *Bifidobacterium* in the feces of the model mice and significantly decrease the number of *Enterobacter, Enterococcus* and *Clostridium perfringens*; Example 1, Example 4 and Example 5 can significantly increase the number of *Lactobacillus* and *Bifidobacterium* in the feces of model mice and significantly decrease the number of *Enterobacter, Enterococcus* and *Clostridium perfringens*. The result shows that the probiotics composition provided by the invention has a synergistic effect, can improve the symptoms of antibiotic-induced diarrhea, and effectively improve the balance of intestinal flora.

The present invention provides a product for regulating intestinal flora, comprising the composition provided by the present invention.

The product for improving intestinal flora is a health care product, a food or a medicament.

The health care product also comprises an acceptable excipient in health care product.

The medicament also comprises a pharmaceutically acceptable excipient.

The food also comprises an acceptable ingredient in food.

The health care product or medicament is an oral preparation, preferably a tablet, a capsule, a pill, a granule, a decoction, a paste, a distillate, an oral liquid, a dripping pill or a syrup.

The present invention provides a composition and use thereof in the manufacture of a product for improving intestinal function. In the present invention, probiotics, prebiotics, *Crataegi Fructus* and *Dioscoreae Rhizoma* are reasonably compounded, wherein each component acts synergistically, thus allowing the composition to have good effects of preventing and/or treating diarrhea as well as improving intestinal flora. The effect thereof is significantly superior to ($P<0.05$) that of the Comparative Examples.

DETAILED EMBODIMENTS OF THE INVENTION

The present invention provides a composition and use thereof in the manufacture of a product for improving intestinal function. Those skilled in the art can use the content herein for reference and suitably modify the process parameters to achieve. It is to be specifically noted that all similar alternatives and modifications will be apparent to those skilled in the art and are considered to be included in the present invention. The method and use of the present invention have been described by way of preferred embodiments, and related personnel obviously can alter or appropriately change and combine the methods and uses described herein so as to realize and apply the technology of the present invention without departing from the content, spirit and scope of the present invention.

All the materials and instruments used in the present invention are ordinary commercial products and are commercially available.

The *Crataegi Fructus* powder is prepared by drying and crushing the fresh fruit of *Crataegi Fructus*, and the particle size is 40 mesh. The *Dioscoreae Rhizoma* powder is prepared by drying and crushing the the *Dioscoreae Rhizoma*, and the particle size is 40 mesh.

The *Lactobacillus* used in the present invention has a bacterial density of no less than 10 billion CFU/g.

The *Bifidobacterium* used in the present invention has a bacterial density of no less than 10 billion CFU/g.

The present invention is further illustrated by the following Examples:

Example 1

20.0 g of *Lactobacillus*, 3.0 g of *Bifidobacterium*, 25.0 g of *Crataegi Fructus* powder, 5.0 g of *Dioscoreae Rhizoma* powder and 47.0 g of inulin.

The above components were pulverized and mixed evenly to prepare a composition.

Example 2

10.0 g of *Lactobacillus*, 5.0 g of *Bifidobacterium*, 5.0 g of *Crataegi Fructus* powder, 15.0 g of *Dioscoreae Rhizoma* powder and 65.0 g of inulin.

The above components were pulverized and mixed evenly to prepare a composition.

Example 3

7.0 g of *Lactobacillus*, 12.0 g of *Bifidobacterium*, 8.0 g of *Crataegi Fructus* powder, 25.0 g of *Dioscoreae Rhizoma* powder and 48.0 g of inulin.

The above components were pulverized and mixed evenly to prepare a composition.

Example 4

2.0 g of *Lactobacillus*, 20.0 g of *Bifidobacterium*, 3.0 g of *Crataegi Fructus* powder, 25.0 g of *Dioscoreae Rhizoma* powder and 50.0 g of inulin.

The above components were pulverized and mixed evenly to prepare a composition.

Example 5

2.0 g of *Lactobacillus*, 2.0 g of *Bifidobacterium*, 3.0 g of *Crataegi Fructus* powder, 3.0 g of *Dioscoreae Rhizoma* powder and 90.0 g of inulin.

The above components were pulverized and mixed evenly to prepare a composition.

Comparative Example 1

50 g of *Crataegi Fructus* powder and 50 g of *Dioscoreae Rhizoma* powder were pulverized and mixed evenly to prepare a composition.

Comparative Example 2

2.0 g of *Lactobacillus*, 2.0 g of *Bifidobacterium*, and 96.0 g of inulin were pulverized and mixed evenly to prepare a composition.

Example 8

The effect of the composition prepared by the composition of the present invention for improving and preventing diarrhea was studied.

1. Experimental Materials 1.1 Experimental Samples and Preparations

Using the compositions prepared in Example 1, Example 4, Example 5 and Comparative Examples 1 to 2 as the experimental samples, the comparative experiments of the Comparative Examples and the Examples were carried out at the same dose. In the experiments, the untreated normal murines were used as the normal controls, and the murines which did not receive the experimental samples after the establishment of the model were used as the model controls, as specifically shown in Table 1:

TABLE 1

Dosage for preventing and improving diarrhea induced by spleen deficiency

| Groups | Administration dosage of the composition (g/kg) |
|---|---|
| Normal control group | Distilled water |
| Model control group | Distilled water |
| Comparative Example 1 | 0.33 |
| Comparative Example 1 | 0.33 |
| Example 1 | 0.33 |

TABLE 1-continued

Dosage for preventing and improving diarrhea induced by spleen deficiency

| Groups | Administration dosage of the composition (g/kg) |
|---|---|
| Example 4 | 0.33 |
| Example 5 | 0.33 |

1.2 Experimental Reagents

Rhubarb root and rhizome, 3% hydrogen peroxide, ampicillin for injection, EMB medium, BDS medium, TPY agar medium, TSC medium, LBS agar and *Enterococcus* agar.

1.3 Experimental Animals

SPF grade SD rats, body weight 180-220 g, male and female in half;

SPF grade BALB/c mice, three weeks of age, male, 18 g~22 g.

1.4 Statistical Analysis of Experimental Results

The experimental data were expressed as mean±SD (x±s). SPSS 16.0 software was used for statistical analysis. Differences between the experimental groups were analyzed by t test, with $P<0.05$ indicating that the difference is statistically significant, and $P<0.01$ indicating that the difference is extremely statistically significant.

2. Experimental Method 2.1 Healthy SD rats were selected and randomly divided into 7 groups, normal control, model control, Comparative Example 1, Comparative Example 2, Example 1, Example 4 and Example 5, with 10 rats in each group.

Except the normal control group, other rats were prepared for establishment of model of spleen deficiency: rhubarb root and rhizome was washed with water to remove dust, and boiled twice in water (boiled for 15 min each time) and filtrated. The two filtrates were combined and concentrated in a water bath to a crude drug concentration of 1 g/ml, and stored in a refrigerator at 4° C. for later use. Animals were normally fed for 3 days, and then administered with rhubarb root and rhizome decoction (1 g/ml) by oral gavage. The administration volume was 1 ml/100 g body weight, twice daily for 10 consecutive days.

After the model establishment, animals were administered according to Table 1, with an oral gavage volume of 1 ml/100 g body weight, once a day for 10 consecutive days; the normal control group and the model control group were administered the same amount of distilled water. Fatigue and huddling, accidie, dull hair color, loose stool and other behaves occurred during the establishment of rhubarb root and rhizome-induced spleen deficiency model. 10 days after establishment of the models, the above symptoms of the model control group were relieved and the fecal characters of rats tended to be normal, while for the animals of Examples 1, Examples 4 and Examples 5, the animal activities and the fecal characters were normal and the dietary and body weight were not significantly different from that of the normal animals.

2. BALB/c mice after one week of acclimating were randomly divided into 7 groups, normal control, model control, Comparative Example 1, Comparative Example 2, Example 1, Example 4 and Example 5, with 15 mice in each group.

The mice were prepared for the antibiotic-associated diarrhea model: mice were administered daily with ampicillin at a dose of 22.4 g/kg (mouse weight) by oral gavage for 5 days, twice daily at a dose of 11.2 g/kg; 5 mice in the normal control group were administered the same volume of saline as the reference. The criteria for the successful establishment of the model are: less luster hair, reduced feed intake, curled up, less activity, unresponsive, slower movement, and clear stain on the buttocks.

On day 6, the mice of each group were observed and weighed after establishment of the model. Mice which were not ideal for the model establishment were removed and ten mice were left in each group. On day 6, experiments for counting loose stools of the mice in each group were carried out before administration: after fasting for 12 h, 25 mL/kg body weight of ampicillin (0.3 g crude drug/mL) was administered to each mouse in each group by oral gavage, and the same amount of physiological saline was administered to the normal control group. The mice were then placed in observation cages for observation, with each animal in a single cage (the bottom of the cage is covered with special filter papers). The number of loose stools, the number of dry stools, and the total number of stools within 5 hours after oral gavage of ampicillin solution (timely replacing the filter papers on the bottom of the cage as appropriate) were recorded, and the loose stool grade of each loose stool and the diarrhea index of each mouse were measured. The judgement standard of dry (formed) stool and loose (wet) stool is based on the absence or presence of stains on the filter paper.

TABLE 2

| Judgement standard of loose stool grade | |
|---|---|
| Diameter of stain (cm) | Loose stool grade |
| <1 | 1 |
| 1-1.9 | 2 |
| 2-2.9 | 3 |
| 3-3.9 | 4 |
| 4-4.9 | 5 |

Calculation formula of loose stool rate: loose stool rate=the number of loose stools/total number of defecation within a certain period of time.

Calculation formula of diarrhea index: diarrhea index=loose stool rate×loose stool grade.

From day 7, the mice in the Comparative Examples and the Examples were treated. The mice were administered with a dose of 0.33 mg/kg by oral gavage once a day, for 14 consecutive days. The diarrhea model control group and the normal control group were administered with the same amount of physiological saline by oral gavage. After 14 days treatment, experiments for counting loose stools were carried out to calculate the loose stool grade, the loose stool rate and the diarrhea index. The results are shown in table 3.

TABLE 3

| | Loose stool grade | | Diarrhea index | |
|---|---|---|---|---|
| | After model establishment (%) | After treatment (%) | After model establishment (%) | After treatment (%) |
| Normal control group | 1.00 ± 0.00*** | 1.00 ± 0.00*** | 0.00 ± 0.00*** | 0.00 ± 0.00*** |
| Model control group | 1.67 ± 0.11 | 1.83 ± 0.10 | 1.42 ± 0.18 | 1.59 ± 0.10 |
| Comparative Example 1 | 1.70 ± 0.09 | 1.58 ± 0.08* | 1.45 ± 0.17 | 1.35 ± 0.06* |
| Comparative Example 2 | 1.66 ± 0.07 | 1.51 ± 0.03** | 1.43 ± 0.15 | 1.30 ± 0.04** |
| Example 1 | 1.71 ± 0.10 | 1.27 ± 0.06*** | 1.45 ± 0.13 | 0.87 ± 0.06*** |
| Example 4 | 1.69 ± 0.09 | 1.29 ± 0.07*** | 1.46 ± 0.16 | 0.90 ± 0.08*** |
| Example 5 | 1.67 ± 0.08 | 1.30 ± 0.05*** | 1.44 ± 0.15 | 0.95 ± 0.05*** |

Note:
Compared with the model control group,
*$P < 0.05$,
**$P < 0.01$,
***$P < 0.001$ It can be known from Table 3 that, the difference between the loose stool grade and diarrhea index of the diarrhea model control group and that of the normal control group is significant ($P<0.05$). Compared with the model control group, the compositions of the Comparative Examples and the Examples were able to decrease the loose stool grade and diarrhea index to some extent, and the difference was significant. Furthermore, the effects of Example 1, Example 4 and Example 5 were significantly superior to that of Comparative Examples 1 and 2 ($p<0.01$). The results show that the compositions provided by the present invention have synergistic effects and may improve the symptoms of antibiotic-induced diarrhea.

Example 8

The effect of the composition prepared by the composition of the present invention for improving and preventing diarrhea was studied.

1. Experimental Materials 1.1 Experimental Samples and Preparations

Using the compositions prepared in Example 1, Example 4, Example 5 and Comparative Examples 1 to 2 as the experimental samples, the experiments of the Comparative Examples and the Examples were carried out at the same dose. In the experiment, the untreated normal animals were used as the normal controls, and the animals which did not receive the experimental samples after the establishment of model were used as the model controls, as specifically shown in Table 4:

TABLE 4

Dose for preventing and improving diarrhea

| Groups | Administration dose of the composition (g/kg) |
|---|---|
| Normal control group | Distilled water |
| Model control group | Distilled water |
| Comparative Example 1 | 0.33 |
| Comparative Example 2 | 0.33 |
| Example 1 | 0.33 |
| Example 4 | 0.33 |
| Example 5 | 0.33 |

1.2 Experimental Reagents

Rhubarb root and rhizome, 3% hydrogen peroxide, ampicillin for injection, EMB medium, BDS medium, TPY agar medium, TSC medium, LBS agar and *Enterococcus* agar.

1.3 Experimental Animals

SPF grade SD rats, body weight 180-220 g, male and female in half;

SPF grade BALB/c mice, three weeks of age, male, 18 g~22 g.

1.4 Statistical Analysis of Experimental Results

The experimental data were expressed as mean±standard deviation (x±s). SPSS 16.0 software was used for statistical analysis. Differences between the experimental groups were analyzed by t test, with P<0.05 indicating that the difference is statistically significant, and P<0.01 meaning that the difference is extremely statistically significant.

2. Experimental Method 2.1 Healthy SD rats were selected and randomly divided into 7 groups, normal control, model control, Comparative Example 1, Comparative Example 2, Example 1, Example 4 and Example 5, with 10 rats in each group.

Except the normal control group, other rats were prepared for establishment of model of spleen deficiency: rhubarb root and rhizome was washed with water to remove dust, and boiled twice in water (boiled for 15 min each time) and filtrated. The two filtrates were combined and concentrated in a water bath to the crude drug concentration of 1 g/ml, and stored in refrigerator at 4° C. for later use. Animals were normally fed for 3 days, and then administered with rhubarb root and rhizome decoction (1 g/ml) by oral gavage. The administration volume was 1 ml/100 g body weight, twice daily for 10 consecutive days.

After the establishment of the model of spleen deficiency, animals were administered according to Table 1, with an oral gavage volume of 1 ml/100 g body weight, once a day for 10 consecutive days; the normal control group and the model control group were administered the same amount of distilled water. After the administration, fresh feces were collected from all groups, and all samples were diluted 10 times in succession. 0.2 mL of each dilution was plated on the LBS, TPY, EMB, *Enterococcus* agar plate and TSC, and incubated at 37° C. under anaerobic conditions. After 48 h incubation, *Lactobacillus, Bifidobacterium, Enterobacter, Enterococcus* and *Clostridium perfringens* were plate-counted.

The results are shown in Table 5:

TABLE 5

Effects of the compositions on the culture of bacteria from feces of spleen deficiency rats (unit: 1 gCFU/g)

| Groups | Bifidobacterium | Lactobacillus | Enterobacter | Enterococcus | Clostridium perfringens |
|---|---|---|---|---|---|
| Normal control group | 8.49 ± 0.20 | 9.26 ± 0.15 | 6.56 ± 0.25 | 3.92 ± 0.46 | 1.09 ± 0.30 |
| Model control group | 7.24 ± 0.18** | 7.60 ± 0.06** | 7.10 ± 0.66 | 3.42 ± 0.39 | 3.48 ± 0.64* |
| Comparative Example 1 | 8.10 ± 0.49 | 8.20 ± 0.08# | 7.77 ± 0.56 | 4.68 ± 0.68 | 2.86 ± 0.61 |
| Comparative Example 2 | 8.32 ± 0.16# | 8.16 ± 0.14# | 7.57 ± 0.51 | 4.77 ± 0.41 | 2.82 ± 0.54 |
| Example 1 | 8.67 ± 0.08## | 9.03 ± 0.23## | 7.61 ± 0.51 | 4.64 ± 0.66 | 2.97 ± 0.61 |
| Example 4 | 8.70 ± 0.09## | 8.89 ± 0.22## | 7.69 ± 0.99 | 4.82 ± 0.39 | 2.91 ± 0.62 |
| Example 5 | 8.57 ± 0.12## | 8.93 ± 0.23## | 7.59 ± 0.98 | 5.03 ± 0.38 | 3.11 ± 0.66* |

Compared with the normal control group,
*P < 0.05,
**P < 0.01;
Compared with the model control group,
P < 0.05,
P < 0.01

The results of culture of the bacterial from the feces of rats (Table 5) show that, compared with the normal control group, the number of *Lactobacillus* and *Bifidobacterium* in stool of spleen deficiency model rats were significantly decreased, and the number of *Clostridium perfringens* increased significantly; Comparative Example 1 can significantly increase the number of *Lactobacillus* in the feces of model rats, but had no significant effect on other bacteria; Comparative Example 2 can significantly increase the number of *Lactobacillus* and *Bifidobacterium* in the feces of the model rats but had no significant effect on other bacteria; Example 1, Example 4 and Example 5 can significantly increase the number of *Lactobacillus* and *Bifidobacterium* in the feces of model rats but had no significant effect on other bacteria, and the effect was significantly superior to that of Comparative Example 1 and 2(P<0.01). The result shows that the probiotics composition provided by the invention has a synergistic effect, can improve the symptoms of diarrhea induced by spleen deficiency, and effectively improve the balance of intestinal flora.

2.2 BALB/c mice after one week of acclimating were randomly divided into 7 groups, normal control, model control, Comparative Example 1, Comparative Example 2, Example 1, Example 4 and Example 5, with 15 mice in each group.

The mice were prepared for the model of antibiotic-associated diarrhea: mice were administered daily with ampicillin at a dose of 22.4 g/kg (mouse weight) by oral gavage for 5 days, twice daily at a dose of 11.2 g/kg; 5 mice in the normal control group were administered the same volume of saline as the reference. The criteria for the successful establishment of the model are: less luster hair, reduced feed intake, curled up, less activity, unresponsive, slower movement of the mice, and clear stain on the buttocks.

On day 6, the mice of each group were observed and weighed after establishment of the model. Mice which were not ideal for the model establishment were removed and ten mice were left in each group. On day 6, experiments for counting loose stools of the mice in each group were carried out before administration: after fasting for 12 h, 25 mL/kg body weight of senna leaf liquid (0.3 g crude drug/mL) was administered to each mouse in each group by oral gavage, and the same amount of physiological saline was administered to the normal control group.

From day 7, the mice in the Comparative Examples and the Examples were treated and studied. The mice were administered with a dose of 0.33 mg/kg by oral gavage once a day, for 14 consecutive days. The diarrhea model control group and the normal control group were administered with the same amount of physiological saline by oral gavage. After 14 days of oral gavage, the stool samples were taken aseptically before and after oral gavage on day 15. All samples were diluted 10 times in succession. 0.2 mL of each dilution was plated on the LBS, TPY, EMB, *Enterococcus* agar plate and TSC, and incubated at 37° C. under anaerobic conditions. After 48 h incubation, *Lactobacillus, Bifidobacterium, Enterobacter, Enterococcus* and *Clostridium perfringens* were plate-counted.

The results are shown in Table 6:

ber of *Lactobacillus* and *Bifidobacterium* in the feces of the model mice, and significantly reduce the number of *Enterococcus* and *Clostridium perfringens*, but had no significant effect on *Enterobacter*; Comparative Example 2 can significantly increase the number of *Lactobacillus* and *Bifidobacterium* in the feces of the model mice and significantly decrease the number of *Enterobacter, Enterococcus* and *Clostridium perfringens*; Example 1, Example 4 and Example 5 can significantly increase the number of *Lactobacillus* and *Bifidobacterium* in the feces of model mice and significantly decrease the number of *Enterobacter, Enterococcus* and *Clostridium perfringens*, and the effect was significantly superior to that of Comparative Examples 1 and 2 ($P<0.01$). The result shows that the probiotics composition provided by the invention has a synergistic effect, can improve the symptoms of antibiotic-induced diarrhea, and effectively improve the balance of intestinal flora.

The foregoings are merely preferred embodiments of the present invention, and it should be noted that an ordinary skilled in the art can make a number of improvements and modifications without departing from the principles of the present invention, and these improvements and modifications should also be deemed to be within the scope of the present invention.

The invention claimed is:

1. A composition, comprising probiotics, prebiotics, *Crataegi fructus* and *Dioscoreae rhizoma*, wherein the mass ratio of the probiotics, the prebiotics, the *Crataegi fructus* and the *Dioscoreae rhizoma* is (2.0-40.0):(30.0-96.0):(1.0-30.0):(1.0-30.0), the probiotics are selected from *Lactobacillus* and *Bifidobacterium*, and the prebiotics are inulin.

TABLE 6

Effects of the compositions on the culture of bacteria from feces of antibiotic induced diarrheal rats (unit: 1 gCFU/g)

| | Group | Bifidobacterium | Lactobacillus | Enterobacter | Enterococcus | Clostridium perfringens |
|---|---|---|---|---|---|---|
| Normal control group | Pre-administration | 7.85 ± 0.23 | 7.22 ± 0.13 | 6.83 ± 0.23 | 4.88 ± 0.17 | 5.68 ± 0.37 |
| | Post-administration | 7.81 ± 0.43 | 7.18 ± 0.41 | 6.87 ± 0.19 | 4.79 ± 0.32 | 5.71 ± 0.46 |
| Model control group | Pre-administration | 5.72 ± 0.18** | 4.88 ± 0.31** | 7.86 ± 0.28** | 6.52 ± 0.23** | 6.99 ± 0.15** |
| | Post-administration | 7.02 ± 0.25*# | 6.18 ± 0.32*# | 7.41 ± 0.52* | 6.26 ± 0.51* | 6.41 ± 0.19* |
| Comparative Example 1 | Pre-administration | 5.71 ± 0.22** | 4.92 ± 0.35** | 7.94 ± 0.46** | 6.54 ± 0.19** | 7.01 ± 0.35** |
| | Post-administration | 7.01 ± 0.37# | 6.45 ± 0.53# | 7.11 ± 0.25 | 5.24 ± 0.46*# | 5.89 ± 0.27# |
| Comparative Example 2 | Pre-administration | 5.75 ± 0.32** | 4.89 ± 0.29** | 7.75 ± 0.31** | 6.53 ± 0.19** | 6.97 ± 0.31** |
| | Post-administration | 7.64 ± 0.54## | 7.23 ± 0.45## | 6.93 ± 0.34# | 4.91 ± 0.20## | 5.93 ± 0.24*# |
| Example 1 | Pre-administration | 5.68 ± 0.31** | 4.85 ± 0.22** | 7.85 ± 0.28** | 6.55 ± 0.15** | 6.95 ± 0.29** |
| | Post-administration | 7.95 ± 0.30### | 7.26 ± 0.42## | 6.90 ± 0.37# | 4.88 ± 0.23## | 5.60 ± 0.19## |
| Example 4 | Pre-administration | 5.74 ± 0.27** | 4.87 ± 0.30** | 7.84 ± 0.43** | 6.53 ± 0.28** | 6.98 ± 0.36** |
| | Post-administration | 7.89 ± 0.25### | 7.28 ± 0.37## | 6.87 ± 0.41# | 4.85 ± 0.33## | 5.63 ± 0.25## |
| Example 5 | Pre-administration | 5.73 ± 0.21** | 4.86 ± 0.18** | 7.82 ± 0.16** | 6.56 ± 0.22** | 7.03 ± 0.26** |
| | Post-administration | 7.87 ± 0.27### | 7.24 ± 0.63## | 6.82 ± 0.19# | 4.91 ± 0.38## | 5.66 ± 0.21## |

Compared with the normal control group,
*$P < 0.05$,
**$P < 0.01$;
Comparison between before and after administration,
$P < 0.05$,
$P < 0.01$,
$p < 0.001$ The results of culture of the bacteria from the feces of mice (Table 6) show that, compared with the normal control group, the number of *Lactobacillus* and *Bifidobacterium* in the feces of antibiotics model mice were significantly decreased, and the number of *Enterobacter, Enterococcus* and *Clostridium perfringens* were significantly increased; Comparative Example 1 can significantly increase the num- 2. The composition according to claim 1, wherein the probiotics are *Lactobacillus* and *Bifidobacterium*, the mass ratio of the *Lactobacillus* to the *Bifidobacterium* is (2.0-20.0):(2.0-20.0).

3. The composition according to claim 1, wherein the probiotics are added in an amount of $10^6$ CFU/g-$10^{12}$ CFU/g based on the total weight of the composition.

4. A method for treating diarrhea, comprising administering the composition of claim 1.

5. The method according to claim 4, wherein the diarrhea is antibiotic-associated diarrhea and/or diarrhea induced by spleen deficiency.

6. A product for treating diarrhea, comprising the composition of claim 1.

7. A method for improving intestinal flora, comprising administering the composition of claim 1.

8. The method according to claim 7, wherein the improving intestinal flora is improving intestinal flora disorder induced by antibiotics administration and/or improving intestinal flora disorder induced by spleen deficiency.

9. A product for improving intestinal flora, comprising the composition of claim 1.

\* \* \* \* \*